(12) United States Patent
Bartelt et al.

(10) Patent No.: US 8,399,713 B2
(45) Date of Patent: *Mar. 19, 2013

(54) ALKYL PERFLUOROALKENE ETHERS

(75) Inventors: Joan Ellen Bartelt, Wilmington, DE (US); Robert D. Lousenberg, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 499 days.

This patent is subject to a terminal disclaimer.

(21) Appl. No.: 12/701,802

(22) Filed: Feb. 8, 2010

(65) Prior Publication Data

US 2010/0209600 A1 Aug. 19, 2010

Related U.S. Application Data

(60) Provisional application No. 61/152,803, filed on Feb. 16, 2009, provisional application No. 61/287,275, filed on Dec. 17, 2009.

(51) Int. Cl.
| | |
|---|---|
| C07C 43/17 | (2006.01) |
| C07C 41/06 | (2006.01) |
| B05D 5/12 | (2006.01) |
| C11D 1/825 | (2006.01) |
| C23G 5/00 | (2006.01) |

(52) U.S. Cl. ........ 568/686; 427/127; 427/240; 427/384; 134/40; 510/506

(58) Field of Classification Search ........................ None
See application file for complete search history.

(56) References Cited

U.S. PATENT DOCUMENTS

| | | | |
|---|---|---|---|
| 3,085,918 | A | 4/1963 | Sherliker et al. |
| 5,908,822 | A | 6/1999 | Dishart |
| 2003/0209685 | A1 | 11/2003 | Robin et al. |
| 2007/0051916 | A1 | 3/2007 | Flynn et al. |
| 2008/0008019 | A1 | 1/2008 | Balasuramanian |
| 2012/0006510 | A1 * | 1/2012 | Bartelt ................ 165/104.11 |

OTHER PUBLICATIONS

Wiley and Simmons, Fluoro Ketones. II. Reactions with Trialkyl Phosphites, Journal of Organic Chemistry, Jul. 1964, vol. 29, Is. 7, pp. 1876-1870.*

Ermolov et al. (Zhurnal Organicheskoi Khimii, 1982, 18(9), 1846-9, astract attached).*

Kurykin, M.A., German L. S. : "Reaction of Trans-Perfluoro-2-Pentene With Alcoholates"; Bulletin of the Academy of Sciences of the USSR, Division of Chemical Science (Translated From Izvestiya Akademii Nauk SSSR, pp. 2647-2650), vol. 11, 1981, pp. 2203-2206, XP002590762.

International Search Report, for International Application No. PCT/US2010/024259, Jul. 2009.

Bekker, Popkova, Snegirev, Knunyants:"Influence of structural factors on stability of fluorine-containing metastable enols." Izvestiya Akademii Nauk SSSR, Seriya Khimicheskaya, vol. 3, 1983, pp. 560-564, XP002610759, Synthesis of VB and VC.

"Dip-Coating of Ultra Thin Liquid Lubricant and Its Thin-Film Magnetic Hard Disks", in IEEE Transactions on Magnetics, vol. 31, No. 6, Nov. 1995.

"Fluorovinylketones From Perfluoropentene-2", David C. England & James S. Piecara, in Journal of Fluorine Chemistry, 28, (1985) pp. 417-423.

* cited by examiner

*Primary Examiner* — Rosalynd Keys

(57) ABSTRACT

Disclosed are compositions comprising a compound having the formula $CF_3(CF_2)_xCF=CFCF(OR)(CF_2)_yCF_3$, wherein R is $CH_3$ or $C_2H_5$ or mixtures thereof, and wherein x and y are independently 0, 1, 2 or 3, and wherein x+y=1, 2 or 3. Also disclosed are unsaturated fluoroethers selected from the group consisting of $CF_3(CF_2)_xCF=CFCF(OR)(CF_2)_yCF_3$, $CF_3(CF_2)_xC(OR)=CFCF_2(CF_2)_yCF_3$, $CF_3CF=CFCF(OR)(CF_2)_x(CF_2)_yCF_3$, $CF_3(CF_2)_xCF=C(OR)CF_2(CF_2)_yCF_3$, and mixtures thereof, wherein R can be either $CH_3$, $C_2H_5$ or mixtures thereof, and wherein x and y are independently 0, 1, 2 or 3, and wherein x+y=0, 1, 2 or 3. Also disclosed herein are novel methods of using a composition comprising at least one of the compounds described above as novel solvents, carrier fluids, dewatering agents, degreasing solvents or defluxing solvents.

30 Claims, No Drawings

ALKYL PERFLUOROALKENE ETHERS

CROSS REFERENCE(S) TO RELATED APPLICATION(S)

This application claims the benefit of priority of U.S. Provisional Applications 61/152,803, filed Feb. 16, 2009, and 61/287,275, filed Dec. 17, 2009.

BACKGROUND INFORMATION

1. Field of the Disclosure

This invention relates to cleaning compositions comprising unsaturated fluorocarbon ethers. The invention further relates to use of said cleaning compositions in methods to clean, degrease, deflux, dewater, and deposit fluorolubricant. The invention further relates to novel unsaturated fluorocarbon ethers and their use as cleaning compositions and in the methods listed above.

2. Description of the Related Art

Chlorofluorocarbon (CFC) compounds have been used extensively in the area of semiconductor manufacture to clean surfaces such as magnetic disk media. However, chlorine-containing compounds such as CFC compounds are considered to be detrimental to the Earth's ozone layer. In addition, many of the hydrofluorocarbons used to replace CFC compounds have been found to contribute to global warming. Therefore, there is a need to identify new environmentally safe solvents for cleaning applications, such as removing residual flux, lubricant or oil contaminants, and particles. There is also a need for identification of new solvents for deposition of fluorolubricants and for drying or dewatering of substrates that have been processed in aqueous solutions.

The present invention provides new compositions comprising unsaturated fluorocarbon ethers, and methods of manufacture of such unsaturated fluorocarbon ethers. These compositions have utility in many of the applications formerly served by CFC compounds. The compositions of the present invention possess some or all of the desired properties of little or no environmental impact, ability to dissolve oils, greases or lubricants (in particular fluorine-containing lubricants), non-flammability, and ability to dissolve surfactant compounds used in methods for drying or dewatering.

SUMMARY

In one embodiment, disclosed here are compositions comprising a compound having the formula $CF_3(CF_2)_xCF=CFCF(OR)(CF_2)_yCF_3$, wherein R is $CH_3$ or $C_2H_5$ or mixtures thereof, and wherein x and y are independently 0, 1, 2 or 3, and wherein x+y=1, 2 or 3.

In another embodiment, disclosed here are compositions comprising a compound having the formula $CF_3(CF_2)_xC(OR)=CFCF_2(CF_2)_yCF_3$, wherein R is $CH_3$ or $C_2H_5$ or mixtures thereof, and wherein x and y are independently 0, 1, 2 or 3, and wherein x+y=1, 2 or 3.

In another embodiment, disclosed herein are compositions comprising a compound having the formula $CF_3CF=CFCF(OR)(CF_2)_x(CF_2)_yCF_3$, wherein R is $CH_3$ or $C_2H_5$ or mixtures thereof, and wherein x and y are independently 0, 1, 2 or 3, and wherein x+y=1, 2 or 3.

In yet another embodiment, disclosed here are compositions comprising a compound having the formula $CF_3(CF_2)_xCF=C(OR)CF_2(CF_2)_yCF_3$, wherein R is $CH_3$ or $C_2H_5$ or mixtures thereof, and wherein x and y are independently 0, 1, 2 or 3, and wherein x+y=1, 2 or 3.

In yet another embodiment, disclosed herein are novel methods of using a composition comprising at least one unsaturated fluoroether selected from the group consisting of $CF_3(CF_2)_xCF=CFCF(OR)(CF_2)_yCF_3$, $CF_3(CF_2)_xC(OR)=CFCF_2(CF_2)_yCF_3$, $CF_3CF=CFCF(OR)(CF_2)_x(CF_2)_yCF_3$, $CF_3(CF_2)_xCF=C(OR)CF_2(CF_2)_yCF_3$, and mixtures thereof, wherein R can be either $CH_3$, $C_2H_5$ or mixtures thereof, and wherein x and y are independently 0, 1, 2 or 3, and wherein x+y=0, 1, 2 or 3.

In yet another embodiment, disclosed herein are novel methods of manufacturing fluorocarbon ethers, including those above.

The foregoing general description and the following detailed description are exemplary and explanatory only and are not restrictive of the invention, as defined in the appended claims.

DETAILED DESCRIPTION

Disclosed herein are compositions comprising compounds having the formula $CF_3(CF_2)_xCF=CFCF(OR)(CF_2)_yCF_3$, wherein R is $CH_3$ or $C_2H_5$ or mixtures thereof, and wherein x and y are independently 0, 1, 2 or 3, and wherein x+y=0, 1, 2 or 3. Also disclosed herein are compositions comprising compounds having the formula $CF_3(CF_2)_xC(OR)=CFCF_2(CF_2)_yCF_3$, wherein R is $CH_3$ or $C_2H_5$ or mixtures thereof, and wherein x and y are independently 0, 1, 2 or 3, and wherein x+y=0, 1, 2 or 3. Also disclosed herein are compositions comprising compounds having the formula $CF_3CF=CFCF(OR)(CF_2)_x(CF_2)_yCF_3$, wherein R is $CH_3$ or $C_2H_5$ or mixtures thereof, and wherein x and y are independently 0, 1, 2 or 3, and wherein x+y=0, 1, 2 or 3. Also disclosed herein are compositions comprising compounds having the formula $CF_3(CF_2)_xCF=C(OR)CF_2(CF_2)_yCF_3$, wherein R is $CH_3$ or $C_2H_5$ or mixtures thereof, and wherein x and y are independently 0, 1, 2 or 3, and wherein x+y=0, 1, 2 or 3.

Also disclosed herein are compositions comprising compounds having the formula $CF_3(CF_2)_xCF=CFCF(OR)(CF_2)_yCF_3$, wherein R is $CH_3$ or $C_2H_5$ or mixtures thereof, and wherein x and y are independently 0, 1, 2 or 3, and wherein x+y=0, 1, 2 or 3 and compounds having the formula $CF_3(CF_2)_xC(OR)=CFCF_2(CF_2)_yCF_3$, wherein R is $CH_3$ or $C_2H_5$, and wherein x and y are independently 0, 1, 2 or 3, and wherein x+y=0, 1, 2 or 3, or mixtures thereof.

In one embodiment, the compounds of the composition are selected from the group consisting of $CF_3(CF_2)_xCF=CFCF(OR)(CF_2)_yCF_3$, $CF_3(CF_2)_xC(OR)=CFCF_2(CF_2)_yCF_3$, $CF_3CF=CFCF(OR)(CF_2)_x(CF_2)_yCF_3$, $CF_3(CF_2)_xCF=C(OR)CF_2(CF_2)_yCF_3$, and mixtures thereof, wherein R can be either $CH_3$, $C_2H_5$ or mixtures thereof, and wherein x and y are independently 0, 1, 2 or 3, and wherein x+y=1, 2 or 3.

In another embodiment, disclosed herein are novel methods of using a composition comprising at least one unsaturated fluoroether selected from the group consisting of $CF_3(CF_2)_xCF=CFCF(OR)(CF_2)_yCF_3$, $CF_3(CF_2)_xC(OR)=CFCF_2(CF_2)_yCF_3$, $CF_3CF=CFCF(OR)(CF_2)_x(CF_2)_yCF_3$, $CF_3(CF_2)_xCF=C(OR)CF_2(CF_2)_yCF_3$, and mixtures thereof, wherein R can be either $CH_3$, $C_2H_5$ or mixtures thereof, and wherein x and y are independently 0, 1, 2 or 3, and wherein x+y=0, 1, 2 or 3.

Many aspects and embodiments have been described above and are merely exemplary and not limiting. After reading this specification, skilled artisans appreciate that other aspects and embodiments are possible without departing from the scope of the invention. Other features and benefits of any one or more of the embodiments will be apparent from the following detailed description, and from the claims.

Before addressing details of embodiments described below, some terms are defined or clarified.

For purposes of the present invention, a phase transfer catalyst is a substance that facilitates the transfer of ionic compounds (e.g., reactants or components) into an organic phase. The phase transfer catalyst facilitates the reaction of these dissimilar and incompatible components. While various phase transfer catalysts may function in different ways, their mechanism of action is not determinative of their utility in the present process.

In one embodiment, the compounds disclosed herein are unsaturated fluoroethers which have utility as novel solvents, carrier fluids, dewatering agents, degreasing solvents or defluxing solvents.

In one embodiment, unsaturated fluoroethers of the invention represent compounds having a formula selected from the group consisting of $CF_3(CF_2)_xCF=CFCF(OR)(CF_2)_yCF_3$, $CF_3(CF_2)_xC(OR)=CFCF_2(CF_2)_yCF_3$, $CF_3CF=CFCF(OR)(CF_2)_x(CF_2)_yCF_3$, $CF_3(CF_2)_xCF=C(OR)CF_2(CF_2)_yCF_3$, and mixtures thereof, wherein R can be either $CH_3$, $C_2H_5$ or mixtures thereof, and wherein x and y are independently 0, 1, 2 or 3, and wherein x+y=1, 2 or 3.

In one embodiment, the compositions disclosed herein may be prepared by contacting a perfluoroalkene, such as perfluoro-3-heptene, pefluoro-2-heptene, perfluoro-2-hexene, perfluoro-3-hexene, or perfluoro-2-pentene with an alcohol in the presence of a strong base. For example, perfluoro-3-heptene may be reacted with an alcohol such as methanol or ethanol, or mixtures thereof, in the presence of an aqueous solution of a strong base to produce unsaturated fluoroethers. Herein after alcohol or "an alcohol" shall be regarded as referring to alcohols such as methanol or ethanol, and to mixtures thereof.

In one embodiment, the products from the reaction of perfluoro-3-heptene with methanol comprise 5-methoxyperfluoro-3-heptene, 3-methoxyperfluoro-3-heptene, 4-methoxyperfluoro-2-heptene and 3-methoxyperfluoro-2-heptene.

In one embodiment, the products from the reaction of perfluoro-2-pentene with methanol comprise 4-methoxyperfluoro-2-pentene, 2-methoxyperfluoro-2-pentene, 3-methoxyperfluoro-2-pentene, and 2-methoxyperfluoro-3-pentene.

In one embodiment, the products from the reaction of perfluoro-2-octene with methanol comprise cis- and trans-2-methoxyperfluoro-2-octene and 2-methoxyperfluoro-3-octene.

In one embodiment, the strong base is a base which will react with an alcohol to produce an alkoxide upon combination of the base with said alcohol. Bases which can be used to form such alkoxides include alkali metal hydroxides, such as sodium hydroxide or potassium hydroxide without limitation.

In one embodiment, the strong base is present in the form of an aqueous solution having a concentration of alkali metal hydroxide of from 10% by weight to 45% by weight. In one embodiment, one mole of alkali metal hydroxide is used per mole of alcohol to produce the alkoxide. In another embodiment, 1.1 moles of alkali metal hydroxide per mole of alcohol is used. In yet another embodiment about 0.9 moles of alkali metal hydroxide per mole of alcohol is used.

In one embodiment, one mole of alkali metal hydroxide is used per mole of perfluoroalkene. In another embodiment, about 1.1 moles of alkali metal hydroxide are used per mole of perfluoroalkene. In yet another embodiment, about 1.05 moles of alkali metal hydroxide are used per mole of perfluoroalkene.

In one embodiment, the alkali metal hydroxide is combined with the pefluoroalkene, and then an alcohol and water are added to the mixture of perfluoroalkene and base, resulting in an immediate exothermic reaction. In another embodiment, the alkali metal hydroxide is dissolved in water and mixed with the perfluoroalkene. Addition of the alcohol results in an immediate exothermic reaction to produce the unsaturated fluoroethers.

In one embodiment, the alcohol is added to the perfluoroalkene, alkali metal hydroxide and water in one portion. In another embodiment, the alcohol is added slowly over a period of time. In one embodiment, the alcohol is added over one hour. In another embodiment, the alcohol is added over two hours. In yet another embodiment, the perfluoroalkene, alkali metal hydroxide and alcohol are added together, and the water is added slowly over time.

In one embodiment, the perfluoroalkene, alkali metal hydroxide, alcohol and water are all added at about room temperature. In another embodiment, the perfluoroalkene and aqueous solution of alkali metal hydroxide are heated to about 50° C., and the alcohol is added slowly over a period of time.

In one embodiment, a phase transfer catalyst is added to the mixture of perfluoroalkene, alkali metal hydroxide, alcohol and water. In one embodiment a phase transfer catalyst is a quaternary ammonium salt. In one embodiment, a phase transfer catalyst is Aliquat 336. In one embodiment, the amount of phase transfer catalyst is from about 1% by weight to about 10% by weight of the alkali metal hydroxide.

The phase transfer catalyst can be ionic or neutral and is selected from the group consisting of crown ethers, onium salts, cryptates and polyalkylene glycols and derivatives thereof, and mixtures thereof. An effective amount of the phase transfer catalyst should be used in order to effect the desired reaction; such an amount can be determined by limited experimentation once the reactants, process conditions and phase transfer catalyst are selected.

Crown ethers are cyclic molecules in which ether groups are connected by dimethylene linkages; the compounds form a molecular structure that is believed to be capable of "receiving" or holding the alkali metal ion of the hydroxide and to thereby facilitate the reaction. Particularly useful crown ethers include 18-crown-6, especially in combination with potassium hydroxide; 15-crown-5, especially in combination with sodium hydroxide; 12-crown-4, especially in combination with lithium hydroxide. Derivatives of the above crown ethers are also useful, e.g., dibenzo-18-crown-6, dicyclohexano-18-crown-6, and dibenzo-24-crown-8 as well as 12-crown-4. Other polyethers particularly useful for alkali metal compounds, and especially for lithium, are described in U.S. Pat. No. 4,560,759 which is incorporated herein by reference to the extent permitted. Other compounds analogous to the crown ethers and useful for the same purpose are compounds which differ by the replacement of one or more of the oxygen atoms by other kinds of donor atoms, particularly N or S, such as hexamethyl-[14]-4,11-diene$N_4$.

Onium salts include quaternary phosphonium salts and quaternary ammonium salts that may be used as the phase transfer catalyst in the process of the present invention; such compounds can be represented by the following formulas I and II:

$$R^1R^2R^3R^4P^{(+)}X'^{(-)} \tag{I}$$

$$R^1R^2R^3R^4N^{(+)}X'^{(-)} \tag{II}$$

wherein each of $R_1$, $R_2$, $R_3$ and $R_4$, which may be the same or different, is an alkyl group, an aryl group or an aralkyl group, and X' is a halogen atom. Specific examples of these compounds include tetramethylammonium chloride, tetramethylammonium bromide, benzyltriethylammonium chloride, methyltrioctylammonium chloride (available commercially under the brands Aliquat 336 and Adogen 464), tetra-n-butylammonium chloride, tetra-n-butylammonium bromide, tetra-n-butylammonium hydrogen sulfate, tetra-n-butylphosphonium chloride, tetraphenylphosphonium bromide, tetraphenylphosphonium chloride, triphenylmethylphosphonium bromide and triphenylmethylphosphonium chloride. Among them, benzyltriethylammonium chloride is preferred for use under strongly basic conditions. Other useful compounds within this class of compounds include those exhibiting high temperature stabilities (e.g., up to about 200.degree. C.) and including 4-dialkylaminopyridinium salts such as tetraphenylarsonium chloride, bis[tris(dimethylamino)phosphine]iminium chloride and tetratris[tris(dimethylamino)phosphinimino]phosphonium chloride; the latter two compounds are also reported to be stable in the presence of hot, concentrated sodium hydroxide and, therefore, can be particularly useful.

Polyalkylene glycol compounds useful as phase transfer catalysts can be represented by the formula:

$$R^6O(R^5O)_tR^7 \quad (III)$$

wherein $R_5$ is an alkylene group, each of $R_6$ and $R_7$, which may be the same or different, is a hydrogen atom, an alkyl group, an aryl group or, an aralkyl group, and t is an integer of at least 2. Such compounds include, for example glycols such as diethylene glycol, triethylenre glycol, tetraethylene glycol, pentaethylene glycol, hexaethylene glycol, diisopropylene glycol, dipropylene glycol, tripropylene glycol, tetrapropylene glycol and tetramethylene glycol, and monoalkyl ethers such as monomethyl, monoethyl, monopropyl and monobutyl ethers of such glycols, dialkyl ethers such as tetraethylene glycol dimethyl ether and pentaethylene glycol dimethyl ether, phenyl ethers, benzyl ethers, and polyalkylene glycols such as polyethylene glycol (average molecular weight about 300) dimethyl ether, polyethylene glycol (average molecular weight about 300) dibutyl ether, and polyethylene glycol (average molecular weight about 400) dimethyl ether. Among them, compounds wherein both $R_6$ and $R_7$ are alkyl groups, aryl groups or aralkyl groups are preferred.

Cryptates are another class of compounds useful in the present as phase transfer catalysts. These are three-dimensional polymacrocyclic chelating agents that are formed by joining bridgehead structures with chains that contain properly spaced donor atoms. For example, bicyclic molecules that result from joining nitrogen bridgeheads with chains of (—OCH$_2$CH$_2$—) groups as in 2.2.2-cryptate (4,7,13,16,21,24-hexaoxa-1,10-diasabicyclo-(8.8.8)hexacosane; available under the brand names cryptand 222 and Kryptofix 222). The donor atoms of the bridges may all be O, N, or S, or the compounds may be mixed donor macrocycles in which the bridge strands contain combinations of such donor atoms.

Combinations of phase transfer catalysts from within one of the groups described above may also be useful as well as combinations or mixtures from more than one group, for example, crown ethers and oniums, or from more than two of the groups, e.g., quaternary phosphonium salts and quaternary ammonium salts, and crown ethers and polyalkylene glycols.

In one embodiment, after several hours the reaction mixture is allowed to cool to ambient temperature and poured into a separatory funnel. The lower organic layer is separated from an aqueous layer containing inorganic salts. The organic layer was then dried, and then could be further purified by distillation. In one embodiment, the organic layer is dried over anhydrous magnesium sulfate. In another embodiment, the organic layer is dried over anhydrous sodium sulfate. In one embodiment of a preparation of perfluoroheptene ethers, a fraction is collected from the distillation predominantly between 108° C. and 122° C., depending on whether the methyl or ethyl ethers were prepared, comprising a mixture of allylic and vinylic perfluoroalkene alkyl ethers.

In one embodiment, the present compositions may further comprise a propellant. Aerosol propellant may assist in delivering the present composition from a storage container to a surface in the form of an aerosol. Aerosol propellant is optionally included in the present composition in up to about 25 weight percent of the total composition. Representative aerosol propellants comprise air, nitrogen, carbon dioxide, difluoromethane (CF$_2$H$_2$, HFC-32), trifluoromethane (CF$_3$H, HFC-23), difluoroethane (CHF$_2$CH$_3$, HFC-152a), trifluoroethane (CH$_3$CF$_3$, HFC-143a; or CHF$_2$CH$_2$F, HFC-143), tetrafluoroethane (CF$_3$CH$_2$F, HFC-134a; or CF$_2$HCF$_2$H, HFC-134), pentafluoroethane (CF$_3$CF$_2$H, HFC-125), 1,3,3,3-tetrafluoro-1-propene (HFO-1234ze), 2,3,3,3-tetrafluoro-1-propene (HFO-1234yf), 1,2,3,3,3-pentafluoropropene (HFO-1225ye), 1,1,3,3,3-pentafluoropropene (HFO-1225ze) and hydrocarbons, such as propane, butanes, or pentanes, or dimethyl ether.

In another embodiment, the present compositions may further comprise at least one surfactant. The surfactants of the present invention include all surfactants known in the art for dewatering or drying of substrates. Representative surfactants include alkyl phosphate amine salts (such as a 1:1 salt of 2-ethylhexyl amine and isooctyl phosphate); ethoxylated alcohols, mercaptans or alkylphenols; quaternary ammonium salts of alkyl phosphates (with fluoroalkyl groups on either the ammonium or phosphate groups); and mono- or di-alkyl phosphates of fluorinated amines. Additional fluorinated surfactant compounds are described in U.S. Pat. No. 5,908,822, incorporated herein by reference.

The amount of surfactant included in the dewatering compositions of the present invention can vary widely depending on the particular drying application in which said composition will be used, but is readily apparent to those skilled in the art. In one embodiment, the amount of surfactant dissolved in the unsaturated fluorinated ether solvent is not greater than about 1 weight percent, based on the total weight of the surfactant/solvent composition. In another embodiment, larger amounts of surfactant can be used, if after treatment with the composition, the substrate being dried is thereafter treated with solvent containing either no or minimal surfactant. In one embodiment, the amount of surfactant is at least about 50 parts per million (ppm, on a weight basis). In another embodiment, the amount of surfactant is from about 100 to about 5000 ppm. In yet another embodiment, the amount of surfactant used is from about 200 to about 2000 ppm based on the total weight of the dewatering composition.

Optionally, other additives may be included in the present compositions comprising solvents and surfactants for use in dewatering. Such additives include compounds having antistatic properties; the ability to dissipate static charge from non-conductive substrates such as glass and silica. Use of an antistatic additive in the dewatering compositions of the present invention may be necessary to prevent spots and stains when drying water or aqueous solutions from electrically non-conductive parts such as glass lenses and mirrors. Most unsaturated fluoroether solvents of the present invention also have utility as dielectric fluids, i.e., they are poor conductors of electric current and do not easily dissipate static charge. Boiling and general circulation of dewatering compositions in conventional drying and cleaning equipment can create static charge, particularly in the latter stages of the drying process where most of the water has been removed from a substrate. Such static charge collects on non-conductive surfaces of the substrate and prevents the release of water from the surface. The residual water dries in place resulting in undesirable spots and stains on the substrate. Static charge remaining on substrates can bring out impurities from the cleaning process or can attract impurities such as lint from the air, which results in unacceptable cleaning performance. In one embodiment, desirable antistatic additives are polar compounds, which are soluble in the present unsaturated fluorinated ether solvent and result in an increase in the conductivity of the unsaturated fluorinated ether solvent resulting in dissipation of static charge from a substrate. In another embodiment, the antistatic additives have a normal boiling point near that of the unsaturated fluorinated ether solvent and have minimal to no solubility in water. In yet another embodiment, the antistatic additives have a solubility in water of less than about 0.5 weight percent. In one embodiment, the solubility of antistatic agent is at least 0.5 weight percent in unsaturated fluorinated ether solvent. In one embodiment, the antistatic additive is nitromethane ($CH_3NO_2$).

In one embodiment, the present dewatering composition containing an antistatic additive is effective in both the dewatering and drying and rinse steps of a method to dewater or dry a substrate as described below.

Another embodiment relates to a method for dewatering or drying a substrate comprising:
a) contacting the substrate with a composition comprising a compound selected from the group consisting of $CF_3(CF_2)_xCF=CFCF(OR)(CF_2)_yCF_3$, $CF_3(CF_2)_xC(OR)=CFCF_2(CF_2)_yCF_3$, $CF_3CF=CFCF(OR)(CF_2)_x(CF_2)_yCF_3$, $CF_3(CF_2)_xCF=C(OR)CF_2(CF_2)_yCF_3$, and mixtures thereof, wherein R can be either $CH_3$, $C_2H_5$ or mixtures thereof, and wherein x and y are independently 0, 1, 2 or 3, and wherein x+y=0, 1, 2 or 3, containing surfactant, thereby dewatering said substrate and
b) recovering the dewatered substrate from the composition.

Many industries use aqueous compositions for the surface treatment of metals, ceramics, glasses, and plastics. Cleaning, plating, and deposition of coatings are often carried out in aqueous media and are usually followed by a step in which residual water is removed. Hot air drying, centrifugal drying, and solvent-based water displacement are methods used to remove such residual water.

While hydrofluorocarbons (HFCs) have been proposed as replacements for the previously used CFC solvents in drying or dewatering applications, many HFCs have limited solvency for water. The use of surfactant, which assists in removal of water from substrates is therefore necessary in many drying or dewatering methods. Hydrophobic surfactants have been added to dewatering or drying solvents to displace water from substrates.

The primary function of the dewatering or drying solvent (unsaturated fluorinated ether solvent) in a dewatering or drying composition is to reduce the amount of water on the surface of a substrate being dried. The primary function of the surfactant is to displace any remaining water from the surface of the substrate. When the unsaturated fluorinated ether solvent and surfactant are combined, a highly effective displacement drying composition is attained.

In one embodiment, the surfactant for dewatering and drying is soluble to at least 1 weight percent based on the total solvent/surfactant composition weight.

In one embodiment, the dewatering or drying method of the present disclosure is very effective in displacing water from a broad range of substrates including metals, such as tungsten, copper, gold, beryllium, stainless steel, aluminum alloys, brass and the like; from glasses and ceramic surfaces, such as glass, sapphire, borosilicate glass, alumina, silica such as silicon wafers used in electronic circuits, fired alumina and the like; and from plastics such as polyolefin ("Alathon", Rynite®, "Tenite"), polyvinylchloride, polystyrene (Styron), polytetrafluoroethylene (Teflon®), tetrafluoroethylene-ethylene copolymers (Tefzel®), polyvinylidenefluoride ("Kynar"), ionomers (Surlyn®), acrylonitrile-butadiene-styrene polymers (Kralac®), phenol-formaldehyde copolymers, cellulosic ("Ethocel"), epoxy resins, polyacetal (Delrin®), poly (p-phenylene oxide) (Noryl®), polyetherketone ("Ultrapek"), polyetheretherketone ("Victrex"), poly(butylene terephthalate) ("Valox"), polyarylate (Arylon®), liquid crystal polymer, polyimide (Vespel®), polyetherimides ("Ultem"), polyamideimides ("Torlon"), poly(p-phenylene sulfide) ("Rython"), polysulfone ("Udel"), and polyaryl sulfone ("Rydel"). In another embodiment, the compositions for use in the present dewatering or drying method are compatible with elastomers.

In one embodiment, the disclosure is directed to a process for removing at least a portion of water from, i.e., dewatering, the surface of a wetted substrate, which comprises contacting the substrate with the aforementioned dewatering composition, and then removing the substrate from contact with the dewatering composition. In one embodiment, water originally bound to the surface of the substrate is displaced by solvent and/or surfactant and leaves with the dewatering composition. By "at least a portion of water" is meant at least about 75 weight percent of water at the surface of a substrate is removed per immersion cycle. By "immersion cycle" is meant one cycle involving at least a step wherein substrate is immersed in the present dewatering composition. Optionally, minimal amounts of surfactant remaining adhered to the substrate can be further removed by contacting the substrate with surfactant-free halocarbon solvent. Holding the article in the solvent vapor or refluxing solvent will further decrease the presence of surfactant remaining on the substrate. Removal of solvent adhering to the surface of the substrate is effected by evaporation. Evaporation of solvent at atmospheric or subatmospheric pressures can be employed and temperatures above and below the boiling point of the halocarbon solvent can be used.

Methods of contacting the substrate with dewatering composition are not critical and can vary widely. For example, the substrate can be immersed in the composition, or the substrate can be sprayed with the composition using conventional equipment. Complete immersion of the substrate is preferred as it generally insures contact between the composition and all exposed surfaces of the substrate. However, any other method, which can easily provide such complete contact may be used.

The time period over which substrate and dewatering composition are contacted can vary widely. Usually, the contacting time is up to about 5 minutes, however, longer times may be used if desired. In one embodiment of the dewatering process, the contacting time is from about 1 second to about 5 minutes. In another embodiment, the contacting time of the dewatering process is from about 15 seconds to about 4 minutes.

Contacting temperatures can also vary widely depending on the boiling point of the composition. In general, the contacting temperature is equal to or less than the composition's normal boiling point.

In one embodiment, the compositions of the present disclosure may further contain a co-solvent. Such co-solvents are desirable where the present compositions are employed in cleaning conventional process residue from substrates, e.g., removing soldering fluxes and degreasing mechanical components comprising substrates of the present invention. Such co-solvents include alcohols (such as methanol, ethanol, isopropanol), ethers (such as diethyl ether, methyl tertiary-butyl ether), ketones (such as acetone), esters (such as ethyl acetate, methyl dodecanoate, isopropyl myristate and the dimethyl or diisobutyl esters of succinic, glutaric or adipic acids or mixtures thereof), ether alcohols (such as propylene glycol monopropyl ether, dipropylene glycol monobutyl ether, and tripropylene glycol monomethyl ether), and hydrocarbons (such as pentane, cyclopentane, hexane, cyclohexane, heptane, octane), and hydrochlorocarbons (such as trans-1,2-dichloroethylene). When such a co-solvent is employed with the present composition for substrate dewatering or cleaning, it may be present in an amount of from about 1 weight percent to about 50 weight percent based on the weight of the overall composition.

In cleaning apparatuses, including vapor degreasing and vapor defluxing equipment, compositions may be lost during operation through leaks in shaft seals, hose connections, soldered joints and broken lines. In addition, the working composition may be released to the atmosphere during maintenance procedures on equipment. If the composition is not a pure component, the composition may change when leaked or discharged to the atmosphere from the equipment, which may cause the composition remaining in the equipment to exhibit unacceptable performance. Accordingly, it is desirable to use as a cleaning composition comprising a single unsaturated fluorinated ether.

In one embodiment, the unsaturated fluoroethers described here further comprise an epoxide as an acid acceptor. In one embodiment, the concentration of such epoxides may range from at least 0.001 weight percent to not more than 1.0 weight percent. In another embodiment, the concentration is from 0.02 weight percent to not more than 0.5 weight percent. In yet another embodiment, to be used at a concentration of not more than 0.2 weight percent of the total composition. The amount of epoxide may range between any combination of these values, inclusive of the recited values.

Examples of suitable expoxides include aliphatic and aromatic epoxides including those selected from epichlorohydrin, 2-hexene epoxide, 3-hexene epoxide, glycidol, prolyene oxide, cis-2,3-pentene oxide, 2-methyl-2,3-epoxybutane, 1,2-epoxycyclopentene, 2,3-dimethyl-2,3-epoxybutane, 1,2-epoxycyclohexane, 1,2-butylene oxide and 2,3-butylene oxide. In another embodiment, the epoxide is a saturate mono-epoxide containing from 3 to 8 carbon atoms.

Another embodiment relates to a method of cleaning a surface comprising:
a. contacting the surface with a composition comprising at least one unsaturated fluoroether selected from the group consisting of $CF_3(CF_2)_xCF\!=\!CFCF(OR)(CF_2)_yCF_3$, $CF_3(CF_2)_xC(OR)\!=\!CFCF_2(CF_2)_yCF_3$, $CF_3CF\!=\!CFCF(OR)(CF_2)_x(CF_2)_yCF_3$, $CF_3(CF_2)_xCF\!=\!C(OR)CF_2(CF_2)_yCF_3$, and mixtures thereof, wherein R can be either $CH_3$, $C_2H_5$ or mixtures thereof, and wherein x and y are independently 0, 1, 2 or 3, and wherein x+y=0, 1, 2 or 3, and
b. recovering the surface from the composition.

In one embodiment, the compositions of the present disclosure are useful as cleaning compositions, cleaning agents, deposition solvents and as dewatering or drying solvents. For proper operation in use, microelectronic components must be cleaned of flux residues, oils and greases, and particulates that may contaminate the surfaces after completion of manufacture. In another embodiment, the present disclosure relates to a process for removing residue from a surface or substrate comprising contacting the surface or substrate with a cleaning composition or cleaning agent of the present invention and, optionally, recovering the surface or substrate substantially free of residue from the cleaning composition or cleaning agent.

In yet another embodiment, the present disclosure relates to a method for cleaning surfaces by removing contaminants from the surface. The method for removing contaminants from a surface comprises contacting the surface having contaminants with a cleaning composition of the present invention to solubilize the contaminants and, optionally, recovering the surface from the cleaning composition. The surface is then substantially free of contaminants.

As stated previously, the contaminants or residues that may be removed by the present method include, but are not limited to oils and greases, flux residues, and particulate contaminants.

In one embodiment of the method, the contacting may be accomplished by spraying, flushing, wiping with a substrate e.g., wiping cloth or paper, that has the cleaning composition incorporated in or on it. In another embodiment of the method, the contacting may be accomplished by dipping or immersing the disk in a bath of the cleaning composition.

In one embodiment of the method, the recovering is by removing the surface that has been contacted from the cleaning composition bath (in a similar manner as described for the method for depositing an a fluorolubricant on a surface as described below). In another embodiment of the method, the recovering is by allowing the cleaning composition that has been sprayed, flushed, or wiped on the disk to drain away. Additionally, any residual cleaning composition that may be left behind after the completion of the previous steps may be evaporated in a manner similar to that for the deposition method as well.

The method for cleaning a surface may be applied to the same types of surfaces as the method for deposition as described below. Semiconductor surfaces or magnetic media disks of silica, glass, metal or metal oxide, or carbon may have contaminants removed by the method. In the method described above, contaminant may be removed from a disk by contacting the disk with the cleaning composition and recovering the disk from the cleaning composition.

In yet another embodiment, the present method also provides methods of removing contaminants from a product, part, component, substrate, or any other article or portion thereof by contacting the article with a cleaning composition of the present invention. For the purposes of convenience, the term "article" is used herein to refer to all such products, parts, components, substrates, and the like and is further intended to refer to any surface or portion thereof. Furthermore, the term "contaminant" is intended to refer to any unwanted material or substance present on the article, even if such substance is placed on the article intentionally. For example, in the manufacture of semiconductor devices it is common to deposit a photoresist material onto a substrate to form a mask for the etching operation and to subsequently remove the photoresist material from the substrate. The term "contaminant" as used herein is intended to cover and encompass such a photo resist material. Hydrocarbon based oils and greases and dioctylphthalate are examples of the contaminants that may be found on the carbon coated disks.

In one embodiment, the present method comprises contacting the article with a cleaning composition of the invention, in a vapor degreasing and solvent cleaning method. In one such embodiment, vapor degreasing and solvent cleaning methods consist of exposing an article, preferably at room temperature, to the vapors of a boiling cleaning composition. Vapors condensing on the object have the advantage of providing a relatively clean, distilled cleaning composition to wash away grease or other contamination. Such processes thus have an additional advantage in that final evaporation of the present cleaning composition from the object leaves behind relatively little residue as compared to the case where the object is simply washed in liquid cleaning composition.

In another embodiment, for applications in which the article includes contaminants that are difficult to remove, the present methods involve raising the temperature of the cleaning composition above ambient or to any other temperature that is effective in such application to substantially improve the cleaning action of the cleaning composition. In one such embodiment, such processes are also generally used for large volume assembly line operations where the cleaning of the article, particularly metal parts and assemblies, must be done efficiently and quickly.

In one embodiment, the cleaning methods of the present invention comprise immersing the article to be cleaned in liquid cleaning composition at an elevated temperature. In another embodiment, the cleaning methods of the present invention comprise immersing the article to be cleaned in liquid cleaning composition at about the boiling point of the cleaning composition. In one such embodiment, this step removes a substantial amount of the target contaminant from the article. In yet another embodiment, this step removes a major portion of the target contaminant from the article. In one embodiment, this step is then followed by immersing the article in freshly distilled cleaning composition, which is at a temperature below the temperature of the liquid cleaning composition in the preceding immersion step. In one such embodiment, the freshly distilled cleaning composition is at about ambient or room temperature In yet another embodiment, the method also includes the step of then contacting the article with relatively hot vapor of the cleaning composition, by exposing the article to vapors rising from the hot/boiling cleaning composition associated with the first mentioned immersion step. In one such embodiment, this results in condensation of the cleaning composition vapor on the article. In certain preferred embodiments, the article may be sprayed with distilled cleaning composition before final rinsing.

It is contemplated that numerous varieties and types of vapor degreasing equipment are adaptable for use in connection with the present methods. One example of such equipment and its operation is disclosed by U.S. Pat. No. 3,085,918, which is incorporated herein by reference. The equipment disclosed therein includes a boiling sump for containing a cleaning composition, a clean sump for containing distilled cleaning composition, a water separator, and other ancillary equipment.

The present cleaning methods may also comprise cold cleaning in which the contaminated article is either immersed in the fluid cleaning composition of the present invention under ambient or room temperature conditions or wiped under such conditions with rags or similar objects soaked in the cleaning composition.

Another embodiment relates to a method of depositing a fluorolubricant on a surface comprising: combining a fluorolubricant and a solvent, said solvent comprising at least one unsaturated fluoroether selected from the group consisting of $CF_3(CF_2)_xCF=CFCF(OR)(CF_2)_yCF_3$, $CF_3(CF_2)_xC(OR)=CFCF_2(CF_2)_yCF_3$, $CF_3CF=CFCF(OR)(CF_2)_x(CF_2)_yCF_3$, $CF_3(CF_2)_xCF=C(OR)CF_2(CF_2)_yCF_3$, and mixtures thereof, wherein R can be either $CH_3$, $C_2H_5$ or mixtures thereof, and wherein x and y are independently 0, 1, 2 or 3, and wherein x+y=0, 1, 2 or 3, to form a lubricant-solvent combination; contacting the combination of lubricant-solvent with the surface; and evaporating the solvent from the surface to form a fluorolubricant coating on the surface The most advanced, highest recording densities and lowest cost method of storing digital information involves writing and reading magnetic flux patterns from rotating disks coated with magnetic materials. A magnetic layer, where information is stored in the form of bits, is sputtered onto a metallic support structure. Next an overcoat, usually a carbon-based material, is placed on top of the magnetic layer for protection and finally a lubricant is applied to the overcoat. A read-write head flies above the lubricant and the information is exchanged between the head and the magnetic layer. In a relentless attempt to increase the efficiency of information transfer, hard drive manufacturers have reduced the distance between the head and the magnetic layer, or fly-height, to less than 100 Angstroms.

Invariably, during normal disk drive application, the head and the disk surface will make contact. To reduce wear on the disk, from both sliding and flying contacts, it must be lubricated.

Fluorolubricants are widely used as lubricants in the magnetic disk drive industry to decrease the friction between the head and disk, that is, reduce the wear and therefore minimize the possibility of disk failure.

There is a need in the industry for improved methods for deposition of fluorolubricants. The use of certain solvents, such as CFC-113 and PFC-5060, has been regulated due to their impact on the environment. Therefore, solvents that will be used in this application should consider environmental impact. Also, such solvent must dissolve the fluorolubricant and form a substantially uniform or uniform coating of fluorolubricant. Additionally, existing solvents have been found to require higher fluorolubricant concentrations to produce a given thickness coating and produce irregularities in uniformity of the fluorolubricant coating.

In one embodiment, the fluorolubricants of the present disclosure comprise perfluoropolyether (PFPE) compounds, or lubricant comprising X-1P®, which is a phosphazene-containing disk lubricant. These perfluoropolyether compounds are sometimes referred to as perfluoroalkylethers (PFAE) or perfluoropolyalkylethers (PFPAE). These PFPE compounds range from simple perfluorinated ether polymers to functionalized perfluorinated ether polymers. PFPE compounds of different varieties that may be useful as fluorolubricant in the present invention are available from several sources. In another embodiment, useful fluorolubricants for the present inventive method include but are not limited to Krytox® GLP 100, GLP 105 or GLP 160 (E. I. du Pont de Nemours & Co., Fluoroproducts, Wilmington, Del., 19898, USA); Fomblin® Z-Dol 2000, 2500 or 4000, Z-Tetraol, or Fomblin® AM 2001 or AM 3001 (sold by Solvay Solexis S.p.A., Milan, Italy); Demnum™ LR-200 or S-65 (offered by Daikin America, Inc., Osaka, Japan); X-1P® (a partially fluorinated hyxaphenoxy cyclotriphosphazene disk lubricant available from Quixtor Technologies Corporation, a subsidiary of Dow Chemical Co, Midland, Mich.); and mixtures thereof. The Krytox® lubricants are perfluoroalkylpolyethers having the general structure $F(CF(CF_3)CF_2O)_n-CF_2CF_3$, wherein n ranges from 10 to 60. The Fomblin® lubricants are functionalized perfluoropolyethers that range in molecular weight from 500 to 4000 atomic mass units and have general formula $X-CF_2-O(CF_2-CF_2-O)_p-(CF_2O)_q-CF_2-X$, wherein X may be $-CH_2OH$, $CH_2(O-CH_2-CH_2)_nOH$, $CH_2OCH_2CH(OH)CH_2OH$ or $-CH_2O-CH_2$-piperonyl. The Demnum™ oils are perfluoropolyether-based oils ranging in molecular weight from 2700 to 8400 atomic mass units.

Additionally, new lubricants are being developed such as those from Moresco (Thailand) Co., Ltd, which may be useful in the present inventive method.

The fluorolubricants of the present invention may additionally comprise additives to improve the properties of the fluorolubricant. X-1P®, which may serve as the lubricant itself, is often added to other lower cost fluorolubricants in order to increase the durability of disk drives by passivating Lewis acid sites on the disk surface responsible for PFPE degradation.

Other common lubricant additives may be used in the fluorolubricants of the present inventive methods.

The fluorolubricants of the present invention may further comprise Z-DPA (Hitachi Global Storage Technologies, San Jose, Calif.), a PFPE terminated with dialkylamine end-groups. The nucleophilic end-groups serve the same purpose as X1P®, thus providing the same stability without any additive.

The surface on which the fluorolubricant may be deposited is any solid surface that may benefit from lubrication. Semiconductor materials such as silica disks, metal or metal oxide surfaces, vapor deposited carbon surfaces or glass surfaces are representative of the types of surfaces for which the methods of the present invention are useful. The present inventive method is particularly useful in coating magnetic media such as computer drive hard disks. In the manufacture of computer disks, the surface may be a glass, or aluminum substrate with layers of magnetic media that is also coated by vapor deposition with a thin (10-50 Angstrom) layer of amorphous hydrogenated or nitrogenated carbon. The fluorolubricant may be deposited on the surface disk indirectly by applying the fluorolubricant to the carbon layer of the disk.

The first step of combining the fluorolubricant and solvent may be accomplished in any suitable manner such as mixing in a suitable container such as a beaker or other container that may be used as a bath for the deposition method. The fluorolubricant concentration in the unsaturated fluorinated ether solvent may be from about 0.010 percent (wt/wt) to about 0.50 percent (wt/wt).

The step of contacting said combination of fluorolubricant and solvent with the surface may be accomplished in any manner appropriate for said surface (considering the size and shape of the surface). A hard drive disk must be supported in some manner such as with a mandrel or some other support that may fit through the hole in the center of the disk. The disk will thus be held vertically such that the plane of the disk is perpendicular to the solvent bath. The mandrel may have different shapes including but not limited to, a cylindrical bar, or a V-shaped bar. The mandrel shape will determine the area of contact with the disk. The mandrel may be constructed of any material strong enough to hold the disk, including but not limited to metal, metal alloy, plastic or glass. Additionally, a disk may be supported vertically upright in a woven basket or be clamped into a vertical position with 1 or more clamps on the outer edge. The support may be constructed of any material with the strength to hold the disk, such as metal, metal alloy, plastic or glass. However the disk is supported, the disk will be lowered into a container holding a bath of the fluorolubricant/solvent combination. The bath may be held at room temperature or be heated or cooled to temperatures ranging from about 0° C. to about 50° C.

Alternatively, the disk may be supported as described above and the bath may be raised to immerse the disk. In either case, the disk may then be removed from the bath (either by lowering the bath or by raising the disk). Excess fluorolubricant/solvent combination can be drained into the bath.

Either of the methods for contacting the fluorolubricant/solvent combination with the disk surface of either lowering the disk into a bath or raising a bath to immerse the disk are commonly referred to as dip coating. Other methods for contacting the disk with the fluorolubricant/solvent combination may be used in the present inventive method, including spraying or spin coating.

When the disk is removed from the bath, the disk will have a coating of fluorolubricant and some residual solvent (unsaturated fluorinated ether) on its surface. The residual solvent may be evaporated. Evaporation is usually performed at room temperature. However, other temperatures both above and below room temperature may be used as well for the evaporation step. Temperatures ranging from about 0° C. to about 100° C. may be used for evaporation.

The surface, or the disk if the surface is a disk, after completion of the coating method, will be left with a substantially uniform or uniform coating of fluorolubricant that is substantially free of solvent. The fluorolubricant may be applied to a thickness of less than about 300 nm, and alternately to a thickness of about 100 to about 300 nm.

A uniform fluorolubricant coating is desired for proper functioning of a disk and so areas of varying fluorolubricant thickness are undesirable on the surface of the disk. As more and more information is being stored on the same size disk, the read/write head must get closer and closer to the disk in order to function properly. If irregularities due to variation in coating thickness are present on the surface of the disk, the probability of contact of the head with these areas on the disk is much greater. While there is a desire to have enough fluorolubricant on the disk to flow into areas where it may be removed by head contact or other means, coating that is too thick may cause "smear," a problem associated with the read/write head picking up excess fluorolubricant.

One specific coating thickness irregularity observed in the industry is that known as the "rabbit ears" effect. These irregularities are visually detected on the surface of the disk after deposition of the fluorolubricant using the existing solvent systems. When the disk is contacted with the solution of fluorolubricant in solvent and then removed from the solution, any points where the solution may accumulate and not drain readily develop drops of solution that do not readily drain off. One such point of drop formation is the contact point (or points) with the mandrel or other support device with the disk. When a V-shaped mandrel is used, there are two contact points at which the mandrel contacts the inside edge of the disk. When solution of fluorolubricant forms drops in these locations that do not drain off when removed from the bath, an area of greater thickness of fluorolubricant is created when the solvent evaporates. The two points of contact with the disk produces what is known as a "rabbit ears" effect, because the areas of greater fluorolubricant thickness produce a pattern resembling rabbit ears visually detectable on the disk surface.

When dip coating is used for depositing fluorolubricant on the surface, the pulling-up speed (speed at which the disk is removed from the bath), and the density of the fluorolubricant and the surface tension are relevant for determining the resulting film thickness of the fluorolubricant. Awareness of these parameters for obtaining the desired film thickness is required. Details on how these parameters effect coatings are given in, "Dip-Coating of Ultra-Thin Liquid Lubricant and its Control for Thin-Film Magnetic Hard Disks" in IEEE Transactions on Magnetics, vol. 31, no. 6, November 1995.

As used herein, the terms "comprises," "comprising," "includes," "including," "has," "having" or any other variation thereof, are intended to cover a non-exclusive inclusion.

For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

EXAMPLES

The concepts described herein will be further described in the following examples, which do not limit the scope of the invention described in the claims.

Example 1

Example 1 Demonstrates the Reaction of Methanol with perfluorohept-3-ene

A 250-mL, 3-neck RB flask was set up with overhead mechanical stirring, reflux condenser, heating mantle, and Claisen with thermocouple well and 50-mL addition funnel. 200 g (125 mL, ~0.57 moles) of perfluorohept-3-ene and 37.7 g (0.67-moles) of powdered KOH were added to the flask. 18.3 g (0.57-moles) of methanol was slowly added with the addition funnel. There was a small exothermic reaction. After stirring for 30-minutes, a small amount of water (~20-mL) was added through the condenser and there was a significant exothermic reaction that increased the temperature to between 60 and 70° C.

After stirring for 2-hours, the reaction mixture was flash distilled under vacuum (100-mmHg) into a dry ice cooled flask. The crude distillate was further separated from water in a 250-mL seperatory funnel and dried over magnesium sulfate. Spinning band distillation resulted in a ~60-mL forerun that boiled predominantly between 54 and 74° C. A second product fraction (~40-mL) was collected starting at 95° C. but boiled predominantly between 108 and 114° C. The second fraction was analyzed by GC-MS and mostly comprised a mixture of alylic and vinylic methyl perfluoroheptene ethers. Saturated methyl monohydrofluoroheptane ether products at about 14% were also part of the mixture. Residual perfluorohept-3-ene comprised about 1% of the distilled mixture.

Example 2

Example 2 Demonstrates the Reaction of Methanol with perfluorohept-3-ene

A second reaction of methanol with perfluorohept-3-ene was done in essentially the same manner as in Example 1. 200-g (125 mL, ~0.57 moles) of perfluorohept-3-ene, 35.3-g (0.63-moles) of powdered KOH, 20-mL of water, and approximately ~1-g of Aliquat® 336 were added to the flask. There was an immediate and substantial exothermic reaction with addition of methanol that increased the temperature to between 60 and 70° C. After addition, stirring and heating to between 60 and 70° C. were continued for 2 hours. After cooling to near ambient temperature, the reaction mixture was poured into a seperatory funnel. There was a significant amount of precipitated salts remaining in the upper aqueous layer. The bottom layer (~120-mL) was isolated and dried over magnesium sulfate.

Example 3

Reaction of Methanol with perfluorohept-3-ene

A third reaction of methanol with perfluorohept-3-ene was done in essentially the same manner as in Example 1. 200-g (125 mL, ~0.57 moles) of perfluorohept-3-ene, 78.3-g (0.63 moles) of 45% aqueous KOH, and 1-g of Aliquat® 336 were added to a 500-mL flask. There was an immediate and substantial exothermic reaction with addition of methanol that increased the temperature to between 60 and 70° C. After addition, stirring and heating to between 60 and 70° C. were continued for 2 hours. After cooling to near ambient temperature, the reaction mixture was poured into a seperatory funnel. There were no precipitated salts remaining in the aqueous layer. The bottom layer (~120-mL) was isolated and dried over magnesium sulfate.

Example 4

Distillation of Methyl Perfluoroheptene Ethers

The crude methyl perfluoroheptene ether products from Examples 2 and 3 were combined, filtered, and distilled by spinning band. An 18-mL first fraction was collected between 54 and 74° C. An intermediate 4-mL fraction was collected between 74° C. and 106° C. A main 180-mL fraction starting at 106° C. that distilled predominantly between 108° C. and 114° C. was collected. A 35-mL still pot fraction remained that was later identified by GC-MS as consisting mainly of higher methanol addition products. Less than 0.1% perfluoroheptene remained in the main fraction. A 25-mL sample was re-distilled by simple distillation. The observed vapor temperature range was 107 to 112° C. The observed still pot temperature range was 110 to 112° C.

Example 5

Reaction of Methanol with perfluoropent-2-ene

A 1-L, 3-neck RB flask was set up with overhead mechanical stirring, water-ice reflux condenser, heating mantle, and Claisen with thermocouple well and 125-mL addition funnel.

382-g (~240 mL, ~1.53 moles) of perfluoropent-2-ene and 219-g (1.76 moles) of aqueous 45% KOH, and ~1-g of Aliquat® 336 were added to the flask. 53.8-g (1.68-moles) of methanol was slowly added with the addition funnel. There was an exothermic reaction that caused the reaction mixture to reflux. The reaction temperature gradually increased from about 24° C. to 60° C. over the course of the methanol addition. After addition, stirring was continued for 2 hours. After cooling to near ambient temperature, the reaction mixture was poured into a seperatory funnel and the two layers slowly separated over 0.5 h. The bottom layer (~240-mL) was isolated and dried over magnesium sulfate.

Example 6

Reaction Ethanol with perfluorohept-3-ene

A 250-mL, 3-neck RB flask was set up with overhead mechanical stirring, reflux condenser, heating mantle, and Claisen with thermocouple well and 50-mL addition funnel. 40-g (0.32-moles) of aqueous KOH and 100-g (0.29 moles) of perfluorohept-3-ene was added to the flask. The mixture was heated with stirring up to 50° C. At that temperature, 16.4-g (0.36 moles) of ethanol, were slowly added to the flask from the addition funnel. An exothermic reaction occurred that caused the reaction mixture to increase in temperature to ~70° C. After the ethanol addition, the reaction mixture was further heated for one hour to maintain the temperature at or near 70° C. Heating was stopped after 1 hour and the reaction was then allowed to cool to near ambient temperature with stirring.

The reaction mixture was poured into a seperatory funnel. The bottom layer (~120-mL) was isolated and dried over magnesium sulfate.

Example 7

Distillation of Ethyl Perfluoroheptene Ethers

The crude ethyl perfluoroheptene ether product from Example 6 was filtered and distilled by spinning band. A 7.5-g first fraction was collected between ~70 and 72° C. A main 73.5-g fraction starting at 110° C. that distilled predominantly between 120° C. and 122° C. was collected. A 5.2-g still pot fraction remained. GC-MS analysis of the main fraction indicated that it consisted of ~62.8% alylic ethyl perfluoroheptene ethers, ~29.7% vinylic ethyl perfluoroheptene ethers, 7.2% ethyl monohydroperfluoroheptane ethers, and 0.3% perfluorohept-3-ene.

Example 8

Reaction of Ethanol with perfluorohept-3-ene

A second reaction of ethanol with perfluorohept-3-ene was done in essentially the same manner as in Example 6 except that 26.3-g (0.57 moles) of ethanol was used and the reaction was not heated prior to addition of ethanol. There was an immediate and substantial exothermic reaction with addition of methanol that increased the temperature to between 60 and 70° C. After addition, stirring and heating to between 60 and 70° C. were continued for 2 hours. After cooling to near ambient temperature, the reaction mixture was poured into a seperatory funnel. The bottom layer was isolated and dried over magnesium sulfate.

Example 9

Distillation of Ethyl Perfluoroheptene Ethers

The crude ethyl perfluoroheptene ether product from Example 8 and the distilled product from Example 7 were combined, filtered, and distilled by spinning band. A main fraction starting at 118° C. up to 123° C. was collected. GC-MS analysis of indicated that it consisted of 60.0% alylic ethyl perfluoroheptene ethers, 33.1% vinylic ethyl perfluoroheptene ethers, 6.4% ethyl monohydroperfluoroheptane ethers, 0.4% unknowns, and 0.05% perfluorohept-3-ene.

Example 10

Reaction of Methanol with perfluorooct-2-ene

A 250 mL, 3-neck RB flask was set up with overhead mechanical stirring, reflux condenser, heating mantle, a Claisen adaptor with thermocouple well, and a PFA fluoropolymer flexible needle that was connected to a 25 cc glass syringe and syringe pump. 64.6 g (162 mmol) of perfluorooct-2-ene, 5.18 g (162 mmol) of methanol, and 0.5 g of Aliquat® 336 were added to the flask. With 400 rpm stirring, a 45% aqueous KOH solution (20.15 g, 162 mmol) was slowly added with the syringe pump at 0.5 mL/min. The reaction was exothermic and the reaction temperature climbed to about 50° C. After the KOH addition was complete, external heating was applied for 2 hours to heat, and maintain, the contents at about 85° C. The reaction was then cooled to near ambient temperature and the crude product (bottom layer, 64.7 g) was separated in a 50 mL funnel. Gas chromatography with mass spectrum detection (GC/MS) of the crude product indicated that the composition was 6.3% perfluorooct-2-ene, 92.3% unsaturated and saturated ethers, and 1.4% higher methanol adducts.

Example 11

Distillation of Methyl Perfluorooctene Ethers

The crude product from Example 10 was dried over magnesium sulfate and filtered using polypropylene filter cloth into a 250-mL still pot. The crude product was distilled using a small spinning band column with a manual valve control. A ~5 mL first fraction was collected between 85° C. and 115° C., followed by a main fraction (48.7 g) starting at 115° C. but quickly rising to 130° C. and boiling predominantly between 133° C. and 135° C. The GC/MS suggested that the main fraction was a 98.2% mixture of primarily unsaturated ethers with some saturated ethers. 1.8% was perfluorooct-2-ene. $^1$H NMR indicated that the saturated ether content was 4.0%. $^{19}$F NMR indicated that the unsaturated ethers were mostly, trans-2-methoxy-perfluorooct-2-ene (44.8%), 2-methoxy-perfluorooct-3-ene (34.5%), and cis-2-methoxy-perfluorooct-2-ene (5.9%).

Example 12

A solvent for depositing a fluorolubricant comprises about 45% $CF_3CF_2CF=CFCF(OCH_3)CF_2CF_3$, 25% $CF_3CF_2C(OCH_3)=CFCF_2CF_2CF_3$ and $CF_3CF_2CF=C(OCH_3)CF_2CF_2CF_3$, 15% $CF_3CF=CFCF(OCH_3)CF_2CF_2CF_3$ and 15% $CF_3CF_2CF(OCH_3)CFHCF_2CF_2CF_3$. This mixture is referred to as Solvent #1.

The ability of Solvent #1 to dissolve a fluorinated oil is determined by adding an amount of the oil to the solvent until the mixture became turbid or spit into two phases. The results in Table 1 show that Solvent #1 has an excellent ability to dissolve the fluorinated oil. In addition, a solution of 0.5 wt % of the oil is prepared. Preweighed metal coupons are dipped into the solution, the solvent evaporated, and the coupon is re-weighed. Table 1 shows the average coating obtained by this dip coating process. Reported coatings weights are the average of three samples. Thus, Solvent #1 can be used as carrier fluid for the deposition of the fluorinated oil onto a substrate.

TABLE 1

| Fluorinated oil | Solubility in solvent | Wt coating obtained |
| --- | --- | --- |
| Krytox GPL 102 oil | miscible | 2.1. ug/cm2 |
| Krytox GPL 106 oil | miscible | 19.3 ug/cm2 |

Example 13

A cleaning solvent comprises about 40% $CF_3CF_2CF=CFCF(OCH_2CH_3)CF_2CF_3$, 35% $CF_3CF_2C(OCH_2CH_3)=CFCF_2CF_2CF_3$ and $CF_3CF_2CF=C(OCH_2CH_3)CF_2CF_2CF_3$, 18% $CF_3CF=CFCF(OCH_2CH_3)CF_2CF_2CF_3$ and 7% $CF_3CF_2CF(OCH_2CH_3)CFHCF_2CF_2CF_3$. This mixture is referred to as Solvent #2.

The ability of Solvent #2 to clean a fluorinated oil off a substrate is determined by preparing metal coupons that are coated in Krytox GPL 106 oil and then cleaning the coupons. After coating the coupon with oil, the coupon is immersed into Solvent #2 at a temperature of about 12° C. for 5 minutes. The weights of the coupon before and after cleaning are measured and the % oil removed is calculated. Results in Table 2 indicate the ability of the solvent to remove the oil and therefore the solvent would be an effective cleaning agent.

TABLE 2

| Coupon | Wt of coupon before coating (g) | Wt of coupon after coating (g) | Wt of coupon after cleaning in Sovent #2 (g) | % Oil removed |
| --- | --- | --- | --- | --- |
| 1 | 10.5213 | 10.6852 | 10.5215 | 99.9 |
| 2 | 10.1318 | 10.2801 | 10.1318 | 100 |
| 3 | 10.4262 | 10.6011 | 10.4267 | 99.7 |

Example 14

The ability of methyl perfluoroheptene ethers (MPHE) to dissolve a fluorinated oil was determined by adding increasing amounts of the oil to the MPHE until the mixture became turbid or spit into two phases. The test showed the oil is miscible in all proportions in the solvent and no turbidity was observed. This is shown in Table 3. In addition, a solution of 5 wt % of the oil was prepared in the MPHE. Preweighed metal coupons with a surface area of 38.7 $cm^2$ were dipped into the solution, the solvent evaporated, and the coupon re-weighed. Table 3 shows the average of 3 coatings obtained by this dip coating process. Thus, MPHE can be used as a carrier fluid for the deposition of the fluorinated oil onto a substrate.

TABLE 3

| Fluorinated oil | Solubility in MPHE | Wt coating obtained (avg of 3) |
| --- | --- | --- |
| Krytox GPL 106 oil | miscible | 115 ug/cm$^2$ |

Example 15

The ability of methyl perfluoropentene ethers (MPPE) to dissolve a fluorinated oil was determined by adding increasing amounts of the oil to the MPPE until the mixture became turbid or spit into two phases. The test showed the oil is miscible in all proportions in the solvent and no turbidity was observed. This is shown in Table 4. In addition, a solution of 5 wt % of the oil was prepared in the MPPE. Preweighed metal coupons with a surface area of 38.7 $cm^2$ were dipped into the solution, the solvent evaporated, and the coupon re-weighed. Table 4 shows the average of 3 coatings obtained by this dip coating process. Thus, MPPE can be used as a carrier fluid for the deposition of the fluorinated oil onto a substrate.

TABLE 4

| Fluorinated oil | Solubility in MPPE | Wt coating obtained (avg of 3) |
| --- | --- | --- |
| Krytox GPL 106 oil | miscible | 162 ug/cm$^2$ |

Example 16

Metal Cleaning with MPPE

Krytox GPL 106 Oil was wiped onto a clean metal coupon, of known weight, with a swab. The weight of the coupon was recorded, and then the coupon was cleaned by immersion into MPPE at the room temperature. The coupon was immersed for 1 minute then air dried. The coupon was then reweighed and the percent of oil removed was determined. These results in Table 5 show that the solvent has excellent efficiency in cleaning fluorinated oils.

TABLE 5

| Coupon | Tare wt (g) | Loaded wt. (g) | Cleaned wt. (g) | Oil removed (%) |
| --- | --- | --- | --- | --- |
| 1 | 21.2749 | 21.3448 | 21.2751 | 99.7 |
| 2 | 21.4979 | 21.6613 | 21.4979 | 100.0 |
| 3 | 21.2876 | 21.4226 | 21.2877 | 99.9 |

Example 17

Metal Cleaning with MPHE

Krytox GPL 106 Oil was wiped onto a clean metal coupon, of known weight, with a swab. The weight of the coupon was recorded, and then the coupon was cleaned by immersion into MPHE at the room temperature. The coupon was immersed for 1 minute then air dried. The coupon was then reweighed and the percent of oil removed was determined. These results in Table 6 show that the solvent has excellent efficiency in cleaning fluorinated oils.

TABLE 6

| Coupon | Tare wt (g) | Loaded wt. (g) | Cleaned wt. (g) | Oil removed (%) |
|---|---|---|---|---|
| 1 | 21.2751 | 21.3352 | 21.2754 | 99.5 |
| 2 | 21.4971 | 21.6585 | 21.5003 | 98.0 |
| 3 | 21.2872 | 21.4339 | 21.2898 | 98.2 |

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A composition comprising at least one unsaturated fluoroether having a formula selected from the group consisting of $CF_3(CF_2)_xCF=CFCF(OR)(CF_2)_yCF_3$, $CF_3(CF_2)_xC(OR)=CFCF_2(CF_2)_yCF_3$, $CF_3CF=CFCF(OR)(CF_2)_x(CF_2)_yCF_3$, and mixtures thereof, wherein R can be either $CH_3$, $C_2H_5$ or mixtures thereof, and wherein x and y are independently 0, 1, 2 or 3, and wherein x+y=1, 2 or 3, except that said unsaturated fluoroether is not $CF_3CF_2CF=C(OCH_3)(CF_2)_2CF_3$.

2. The composition of claim 1, wherein the unsaturated fluoroether comprises a compound having the formula $CF_3(CF_2)_xCF=CFCF(OR)(CF_2)_yCF_3$, wherein R is $CH_3$ or $C_2H_5$ or mixtures thereof, and wherein x and y are independently 0, 1, 2 or 3, and wherein x+y=1, 2 or 3.

3. The composition of claim 2, further comprising a compound having the formula $CF_3(CF_2)_xC(OR)=CFCF_2(CF_2)_yCF_3$, wherein R is $CH_3$ or $C_2H_5$ or mixtures thereof, and wherein x and y are independently 0, 1, 2 or 3, and wherein x+y=1, 2 or 3.

4. The composition of claim 1, wherein the unsaturated fluoroether comprises a compound having the formula $CF_3(CF_2)_xC(OR)=CFCF_2(CF_2)_yCF_3$, wherein R is $CH_3$ or $C_2H_5$ or mixtures thereof, and wherein x and y are independently 0, 1, 2 or 3, and wherein x+y=1, 2 or 3, except that when x=2 and R is $CH_3$, y does not equal 0.

5. The composition of claim 1, wherein the unsaturated fluoroether comprises a compound having the formula $CF_3CF=CFCF(OR)(CF_2)_x(CF_2)_yCF_3$, wherein R is $CH_3$ or $C_2H_5$ or mixtures thereof, and wherein x and y are independently 0, 1, 2 or 3, and wherein x+y =1, 2 or 3.

6. The composition of claim 2, wherein R is $C_2H_5$.

7. The composition of claim 2 wherein R is $CH_3$.

8. A method for removing residue from a surface comprising:
   a. contacting the surface with a composition comprising at least one unsaturated fluoroether selected from the group consisting of $CF_3(CF_2)_xCF=CFCF(OR)(CF_2)_yCF_3$, $CF_3(CF_2)_xC(OR)=CFCF_2(CF_2)_yCF_3$, $CF_3CF=CFCF(OR)(CF_2)_x(CF_2)_yCF_3$, $CF_3(CF_2)_xCF=C(OR)CF_2(CF_2)_yCF_3$, and mixtures thereof, wherein R can be either $CH_3$, $C_2H_5$ or mixtures thereof, and wherein x and y are independently 0, 1, 2 or 3, and wherein x+y=0, 1, 2 or 3;
   b. recovering the surface from the composition.

9. The method of claim 8 wherein said composition further comprises a propellant.

10. The method of claim 9 wherein said propellant is selected from the group consisting of air, nitrogen, carbon dioxide, difluoromethane ($CF_2H_2$, HFC-32), trifluoromethane ($CF_3H$, HFC-23), difluoroethane ($CHF_2CH_3$, HFC-152a), trifluoroethane ($CH_3CF_3$, HFC-143a; or $CHF_2CH_2F$, HFC-143), tetrafluoroethane ($CF_3CH_2F$, HFC-134a; or $CF_2HCF_2H$, HFC-134), pentafluoroethane ($CF_3CF_2H$, HFC-125), 1,3,3,3-tetrafluoro-1-propene (HFO-1234ze), 2,3,3,3-tetrafluoro-1-propene (HFO-1234yf), 1,2,3,3,3-pentafluoropropene (HFO-1225ye), 1,1,3,3,3-pentafluoropropene (HFO-1225ze), hydrocarbons, and dimethyl ether.

11. The method of claim 8 wherein said composition further comprises at least one surfactant.

12. The method of claim 8 wherein said contacting is accomplished by vapor degreasing.

13. The method of claim 12, wherein the vapor degreasing is performed by:
   a. Boiling the composition; and
   b. Exposing the article to vapors of the boiling cleaning composition.

14. The method of claim 8, wherein the contacting is accomplished by immersing the article in said composition, wherein the composition is at a temperature greater than ambient or room temperature.

15. The method of claim 14, wherein the composition is at a temperature of about the boiling point of the composition.

16. The method of claim 14 comprising, after immersing the article in the composition, the further step of immersing the article in the composition, wherein the composition is at a temperature lower than that of the first immersing step.

17. The method of claim 16, wherein the composition in the second immersing step is at ambient or room temperature.

18. The method of claim 16 comprising, after the second immersing step, the further steps of boiling the composition and exposing the article to vapors of the boiling composition.

19. The method of claim 8, wherein the composition is at ambient or room temperature.

20. The method of claim 8, wherein the contacting is accomplished by wiping the article with an object soaked in the composition.

21. A method for depositing a fluorolubricant on a surface comprising:
   a. combining a fluorolubricant and a solvent, said solvent comprising at least one unsaturated fluoroether selected from the group consisting of $CF_3(CF_2)_xCF=CFCF(OR)(CF_2)_yCF_3$, $CF_3(CF_2)_xC(OR)=CFCF_2(CF_2)_yCF_3$, $CF_3CF=CFCF(OR)(CF_2)_x(CF_2)_yCF_3$, $CF_3(CF_2)_xCF=C(OR)CF_2(CF_2)_yCF_3$, and mixtures thereof, wherein R can be either $CH_3$, $C_2H_5$ or mixtures thereof, and wherein x and y are independently 0, 1, 2 or 3, and wherein x+y=0, 1, 2 or 3, to form a lubricant-solvent combination;
b. contacting the combination of lubricant-solvent with the surface; and
c. evaporating the solvent from the surface to form a fluorolubricant coating on the surface.

22. The method of claim 21, wherein the surface is that of a semiconductor material, metal, metal oxide, vapor deposited carbon, or glass.

23. The method of claim 22, wherein the surface is that of a magnetic medium.

24. The method of claim 23, wherein the magnetic medium is a computer disk.

25. The method of claim 21, wherein the contacting step is accomplished by dipping or immersing the surface in a bath comprising the fluorolubricant.

26. The method of claim 21, wherein the contacting step is accomplished by spraying or spin coating the surface with the fluorolubricant.

27. The method of claim 21, wherein the fluorolubricant concentration in the lubricant-solvent combination is from about 0.02 weight percent to about 0.5 weight percent.

28. The method of claim 21, wherein the evaporating step is accomplished at a temperature of from about 10° C. to about 40° C.

29. The method of claim 21, wherein the fluorolubricant comprises a perfluoropolyether.

30. The method of claim 21, wherein the fluorolubricant is selected from the group consisting of perfluoropolyethers and mixtures thereof.

* * * * *